(12) United States Patent
Shirata et al.

(10) Patent No.: US 9,329,119 B2
(45) Date of Patent: May 3, 2016

(54) SPEED REDUCER FOR INDUSTRIAL ROBOT

(75) Inventors: Takuya Shirata, Tokyo (JP); Kenichi Fujimoto, Tsu (JP)

(73) Assignee: NABTESCO CORPORATION, Tokyo (JP)

( * ) Notice: Subject to any disclaimer, the term of this patent is extended or adjusted under 35 U.S.C. 154(b) by 0 days.

(21) Appl. No.: 13/991,132

(22) PCT Filed: Dec. 2, 2011

(86) PCT No.: PCT/JP2011/077980
§ 371 (c)(1),
(2), (4) Date: May 31, 2013

(87) PCT Pub. No.: WO2012/074112
PCT Pub. Date: Jun. 7, 2012

(65) Prior Publication Data
US 2013/0250303 A1    Sep. 26, 2013

(30) Foreign Application Priority Data

Dec. 2, 2010 (JP) .................................. 2010-269097
Jan. 12, 2011 (JP) .................................. 2011-003853

(51) Int. Cl.
*G01N 21/64* (2006.01)
*G01N 21/25* (2006.01)
(Continued)

(52) U.S. Cl.
CPC ................ *G01N 21/25* (2013.01); *B25J 9/102* (2013.01); *B25J 13/087* (2013.01);
(Continued)

(58) Field of Classification Search
CPC ....... B25J 13/087; B25J 19/0062; B25J 9/102
USPC .......................... 356/319, 326, 332, 409, 410
See application file for complete search history.

(56) References Cited

U.S. PATENT DOCUMENTS 2,580,500 A    1/1952   Albert
3,692,410 A    9/1972   Jurany et al.
(Continued)

FOREIGN PATENT DOCUMENTS

JP    S53-124988 U    10/1978
JP    60-224043 A     11/1984
(Continued)

OTHER PUBLICATIONS

International Search Report; PCT/JP2011/077980; Mar. 6, 2012.
(Continued)

*Primary Examiner* — Michael A Lyons
*Assistant Examiner* — Maurice Smith
(74) *Attorney, Agent, or Firm* — Studebaker & Brackett PC

(57) ABSTRACT

A speed reducer for an industrial robot includes a speed reducer main body and a lubricant deterioration sensor for detecting deterioration of a lubricant in the speed reducer main body. The lubricant deterioration sensor includes a light emitting element for emitting light, a color light receiving element for detecting a color of received light, a clearance forming member forming an oil clearance in which the lubricant enters, and a support member supporting the light emitting element, the color light receiving element, and the clearance forming member. The clearance forming member is transmissive so that the light emitted from the light emitting element transmits therethrough. The oil clearance is provided on an optical path from the light emitting element to the color light receiving element.

13 Claims, 13 Drawing Sheets

(51) Int. Cl.
*G01N 33/28* (2006.01)
*B25J 9/10* (2006.01)
*B25J 13/08* (2006.01)
*B25J 19/00* (2006.01)
*F16H 57/04* (2010.01)
*G01N 21/85* (2006.01)

(52) U.S. Cl.
CPC ........ *B25J 19/0062* (2013.01); *F16H 57/0405* (2013.01); *G01N 33/2888* (2013.01); *G01N 21/251* (2013.01); *G01N 21/85* (2013.01)

(56) References Cited

U.S. PATENT DOCUMENTS

| | | | |
|---|---|---|---|
| 4,040,743 | A | 8/1977 | Villaume et al. |
| 4,114,038 | A | 9/1978 | Parker |
| 4,171,909 | A | 10/1979 | Kramer et al. |
| 4,534,651 | A | 8/1985 | Minikane |
| 4,851,665 | A | 7/1989 | Pesavento et al. |
| 5,001,938 | A | 3/1991 | Downie |
| 5,007,740 | A | 4/1991 | Jeannotte et al. |
| 5,069,524 | A * | 12/1991 | Watanabe et al. ............ 385/59 |
| 5,121,110 | A * | 6/1992 | Mahar et al. ............ 340/693.9 |
| 5,181,082 | A | 1/1993 | Jeannotte et al. |
| 5,194,910 | A | 3/1993 | Kirkpatrick et al. |
| 5,208,465 | A * | 5/1993 | Jacobson ..................... 250/573 |
| 5,293,107 | A * | 3/1994 | Akeel ..................... 318/568.11 |
| 5,371,600 | A | 12/1994 | Hsia et al. |
| 5,402,241 | A | 3/1995 | Jeannotte et al. |
| 5,404,217 | A | 4/1995 | Janik et al. |
| 5,530,553 | A | 6/1996 | Hsia et al. |
| 5,567,306 | A * | 10/1996 | DeWachter ............. 210/167.02 |
| 5,729,006 | A | 3/1998 | Maeda |
| 6,546,814 | B1 * | 4/2003 | Choe et al. ................. 73/862.08 |
| 7,027,160 | B2 | 4/2006 | Sperling |
| 7,339,657 | B2 * | 3/2008 | Coates ............................ 356/73 |
| 7,612,874 | B2 * | 11/2009 | Kong et al. ..................... 356/70 |
| 7,916,299 | B2 | 3/2011 | Trump et al. |
| 8,155,891 | B2 | 4/2012 | Kong et al. |
| 8,379,192 | B2 | 2/2013 | Mannhardt et al. |
| 8,493,561 | B2 | 7/2013 | Park et al. |
| 8,542,363 | B2 | 9/2013 | Wynn et al. |
| 8,648,321 | B2 | 2/2014 | Schenkel et al. |
| 2002/0005954 | A1 | 1/2002 | Sperling |
| 2002/0162407 | A1 * | 11/2002 | Nightlinger et al. ............. 74/1.5 |
| 2003/0142316 | A1 | 7/2003 | Schenkl et al. |
| 2004/0233431 | A1 * | 11/2004 | Ganz et al. .................... 356/338 |
| 2005/0066707 | A1 * | 3/2005 | Katsuki et al. ............... 73/23.21 |
| 2007/0046936 | A1 * | 3/2007 | Mauzy et al. ................. 356/328 |
| 2008/0024761 | A1 | 1/2008 | Kong et al. |
| 2009/0036250 | A1 | 2/2009 | Koyama et al. |
| 2009/0086212 | A1 * | 4/2009 | Kitamura ..................... 356/460 |
| 2009/0140754 | A1 | 6/2009 | Schenkl et al. |
| 2009/0216464 | A1 | 8/2009 | Kong et al. |
| 2009/0228239 | A1 * | 9/2009 | Inoue et al. ................... 702/184 |
| 2009/0279072 | A1 * | 11/2009 | Arakawa ......................... 356/70 |
| 2010/0027015 | A1 | 2/2010 | Schweng et al. |
| 2010/0157304 | A1 | 6/2010 | Takahashi et al. |
| 2012/0033303 | A1 * | 2/2012 | Nagaoka ................ G02B 7/021 359/601 |
| 2012/0038925 | A1 | 2/2012 | Gahr et al. |
| 2012/0162650 | A1 | 6/2012 | Wynn et al. |
| 2012/0162652 | A1 | 6/2012 | Schenkl et al. |
| 2013/0250281 | A1 | 9/2013 | Shirata |
| 2013/0250303 | A1 | 9/2013 | Shirata et al. |
| 2014/0146307 | A1 | 5/2014 | Arrondo et al. |

FOREIGN PATENT DOCUMENTS

| | | | |
|---|---|---|---|
| JP | 63-184040 | A | 7/1988 |
| JP | 63184040 | A * | 7/1988 ............. G01N 21/59 |
| JP | H01-501247 | A | 4/1989 |
| JP | 01-119741 | A | 5/1989 |
| JP | 06-182649 | A | 7/1994 |
| JP | 07-118778 | A | 5/1995 |
| JP | 07-146233 | A | 6/1995 |
| JP | 08-086751 | A | 4/1996 |
| JP | 08-126369 | A | 5/1996 |
| JP | 10-104160 | A | 4/1998 |
| JP | H11-271217 | A | 10/1999 |
| JP | 2000-146696 | A | 5/2000 |
| JP | 2001-242079 | A | 9/2001 |
| JP | 2002-006039 | A | 1/2002 |
| JP | 2007-198767 | A | 8/2007 |
| JP | 2007-278903 | A | 10/2007 |
| JP | 2009-226488 | A | 10/2009 |
| JP | 4523977 | B2 | 8/2010 |
| JP | 2012-143837 | A | 8/2012 |
| WO | 88/02109 | A1 | 3/1988 |
| WO | 99/49302 | A1 | 9/1999 |
| WO | 2007/091568 | A1 | 8/2007 |

OTHER PUBLICATIONS

International Search Report; PCT/JP2011/077977; Mar. 6, 2012.
Non-Final Office Action issued by the U.S Patent Office on Sep. 24, 2014, which is related to U.S. Appl. No. 13/991,133.
An Office Action; "Notification of Reasons for Refusal," issued by the Japanese Patent Office on Nov. 6, 2014, which corresponds to Japanese Patent Application No. 2010-269097 and is related to U.S. Appl. No. 13/991,132; with English language translation.
An Office Action; "Notification of Reasons for Refusal," issued by the Japanese Patent Office on Nov. 18, 2014, which corresponds to Japanese Patent Application No. 2011-003853 and is related to U.S. Appl. No. 13/991,132; with English language translation.
Non-Final Office Action issued by the U.S Patent Office on Jan. 5, 2016, which corresponds to U.S. Appl. No. 14/952,355 and is related to U.S. Appl. No. 13/991,132.
An Office Action; "Final Rejection," issued by the Japanese Patent Office on Jul. 1, 2015, which corresponds to Japanese Patent Application No. 2010-269097 and is related to U.S. Appl. No. 13/991,132; with English language translation.
An Office Action; "Final Rejection," issued by the Japanese Patent Office on Jun. 17, 2015, which corresponds to Japanese Patent Application No. 2011-003853 and is related to U.S. Appl. No. 13/991,132; with English language translation.

* cited by examiner

SPEED REDUCER FOR INDUSTRIAL ROBOT

TECHNICAL FIELD

The invention relates to a speed reducer for an industrial robot capable of predicting occurrence of a failure.

BACKGROUND ART

A speed reducer is used in a joint of an industrial robot, and accuracy of a trajectory of an arm is greatly dependent on performance of the speed reducer. When the performance of the speed reducer for the industrial robot is deteriorated, appropriate replacement of the speed reducer is of importance. However, when the speed reducer for the industrial robot is replaced, an industrial robot outfitted with the speed reducer for an industrial robot and a production line where the industrial robot is installed must be stopped. Accordingly, in order to ascertain a time to replace the speed reducer for an industrial robot, an appropriate prediction of a failure in the speed reducer for the industrial robot is of great importance.

A technique which has hitherto been known as a technique for predicting occurrence of a failure in the speed reducer for an industrial robot is to take a sample of a lubricant of the speed reducer, magnetically detect a concentration of iron powder, and predict occurrence of a failure in the speed reducer from the thus-detected concentration of iron powder (see; for instance, Patent Document 1).

CITATION LIST

Patent Document

Patent Document 1: JP-B-4523977

SUMMARY OF INVENTION

Technical Problem

However, the related-art technique requires to detect an amount of iron powder by taking a sample of lubricant from the speed reducer and, hence, has a problem that instancy is inferior.

Accordingly, an object of the invention is to provide a speed reducer for an industrial robot capable of instantly predicting occurrence of a failure.

Solution to Problem

A speed reducer for an industrial robot according to the present invention includes:

a speed reducer main body; and a lubricant deterioration sensor for detecting deterioration of a lubricant in the speed reducer main body, wherein the lubricant deterioration sensor includes a light emitting element for emitting light, a color light receiving element for detecting a color of received light, a clearance forming member forming an oil clearance in which the lubricant enters, and a support member supporting the light emitting element, the color light receiving element, and the clearance forming member, the clearance forming member is transmissive so that the light emitted from the light emitting element transmits therethrough, and the oil clearance is provided on an optical path from the light emitting element to the color light receiving element.

By means of the configuration, the lubricant deterioration sensor detects colors of light, among light rays emitted from the light emitting element, of wavelengths that are not absorbed by contaminants in a lubricant, such as iron powder, by means of the color light receiving element at the oil clearance. Hence, colors of the contaminants in the lubricant in the speed reducer main body can be instantly detected. Specifically, the lubricant deterioration sensor can instantly specify types and amounts of contaminants in the lubricant of the speed reducer main body on the basis of the colors detected by the color light receiving element. As a consequence, the speed reducer for an industrial robot of the invention can instantly predict occurrence of a failure.

In the speed reducer for an industrial robot according to the present invention, the light emitting element may be a white LED configured to emit white light.

By means of the above configuration, when compared with a configuration in which the light emitting elements are lamps except; for instance, LEDs, the sensor can be miniaturized. Therefore, the speed reducer for an industrial robot of the invention can be miniaturized.

In the speed reducer for an industrial robot according to the present invention, a reflection surface for bending the optical path may be formed on the clearance forming member.

By means of the above configuration, when compared with a configuration where the optical path from the light emitting element to the color light receiving element is straightforward, the light emitting element and the color light receiving element are placed in close proximity to each other, so that the entirety of the lubricant deterioration sensor can be made compact. Further, in the lubricant deterioration sensor, the clearance forming member plays the role of bending the optical path as well as the role of creating the oil clearance. Hence, when compared with a configuration separately provided with a member for bending the optical path instead of the clearance forming member, the number of parts can be curtailed. Consequently, the speed reducer for an industrial robot of the invention can be miniaturized and subjected to a decrease in the number of parts.

In the speed reducer for an industrial robot according to the present invention, the clearance forming member may have two rectangular prisms each of which has the reflection surface for bending the optical path at 90-degree angle, so that the optical path is bent at 180-degree by the reflection surfaces of the two rectangular prisms, and the oil clearance may be formed between the two rectangular prisms.

By means of the configuration, the lubricant deterioration sensor can be miniaturized by means of a simple configuration that includes a smaller number of parts. Consequently, the speed reducer for an industrial robot of the invention can be miniaturized by means of a simple configuration that includes a smaller number of parts.

In the speed reducer for an industrial robot according to the present invention may further includes an optical path surrounding member for surrounding at least a portion of the optical path, wherein a surface of the optical path surrounding member is treated with antireflection processing.

By means of the configuration, in the lubricant deterioration sensor, the color light receiving element prevents from receiving unwanted reflected light. Hence, when compared with a configuration in which the color light receiving element experiences unwanted reflected light, detection accuracy of colors of contaminants in the lubricant can be enhanced. Therefore, the speed reducer for an industrial robot of the invention can enhance the accuracy of prediction of a failure.

In the speed reducer for an industrial robot according to the present invention, the surfaces of the clearance forming member that forms the oil clearance may be treated with oil repellent treatment.

By means of the configuration, the lubricant deterioration sensor enables easy circulation of the lubricant through the oil clearance. Therefore, when compared with a configuration in which the lubricant becomes easily congested in the oil clearance, the detection accuracy of colors of contaminants in the lubricant can be enhanced. Moreover, in relation to the lubricant deterioration sensor, when the surfaces that make up the oil clearance are given oil repellent treatment, the surfaces that make up the oil clearance become less susceptible to stains, so that degradation of detection accuracy of colors of contaminants in the lubricant, which would otherwise be caused by adhesion of stains on the surfaces, can be inhibited. Therefore, the speed reducer for an industrial robot of the invention can enhance the accuracy of prediction of a failure.

An industrial robot according to the present invention includes:

an arm;

a speed reducer for a joint of the arm; and a lubricant deterioration sensor for detecting deterioration of a lubricant of the speed reducer, wherein the lubricant deterioration sensor has a light emitting element for emitting light, a color light receiving element for detecting a color of received light, a clearance forming member forming an oil clearance in which the lubricant enters, and a support member supporting the light emitting element, the color light receiving element, and the clearance forming member, the clearance forming member is transmissive so that the light emitted from the light emitting element transmits therethrough, and the oil clearance is provided on an optical path from the light emitting element to the color light receiving element.

By means of the configuration, the lubricant deterioration sensor detects colors of light, among light rays emitted from the light emitting element, of wavelengths that are not absorbed by contaminants in a lubricant, such as iron powder, by means of the color light receiving element at the oil clearance. Hence, colors of the contaminants in the lubricant in the speed reducer main body can be instantly detected. Specifically, the lubricant deterioration sensor can instantly specify types and amounts of contaminants in the lubricant of the speed reducer on the basis of the colors detected by the color light receiving element. As a consequence, the industrial robot of the invention can instantly predict occurrence of a failure.

Advantageous Effects of Invention

The speed reducer for an industrial robot of the invention enables instant prediction of a failure.

DESCRIPTION OF EMBODIMENTS

An embodiment of the invention is hereunder described by reference to the drawings.

First, a configuration of an industrial robot of the embodiment is described.

Figure 1:
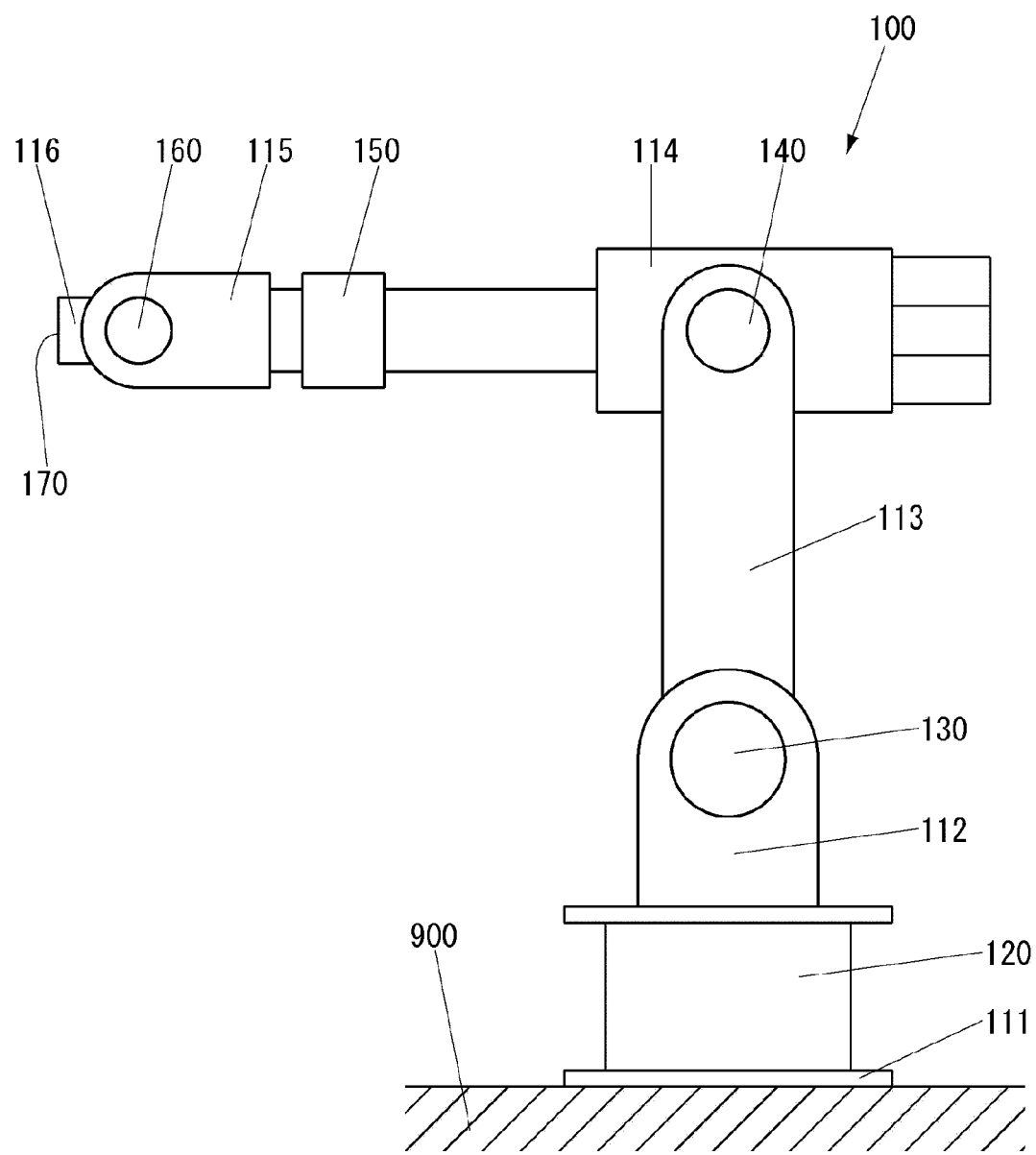
FIG. 1 is a side view of an industrial robot of an embodiment of the invention.

FIG. 1 is a side view of an industrial robot 100 of the embodiment.

As show in FIG. 1, the industrial robot 100 has a mount 111 that is mounted to an installation area 900, such as a floor and a ceiling; arms 112 to 116; a joint 120 for joining the mount 111 to the arm 112; a joint 130 for joining the arm 112 to the arm 113; a joint 140 for joining the arm 113 to the arm 114; a joint 150 for joining the arm 114 to the arm 115; a joint 160 for joining the arm 115 to the arm 116; and a joint 170 for joining the arm 116 to an unillustrated hand.

Figure 2:
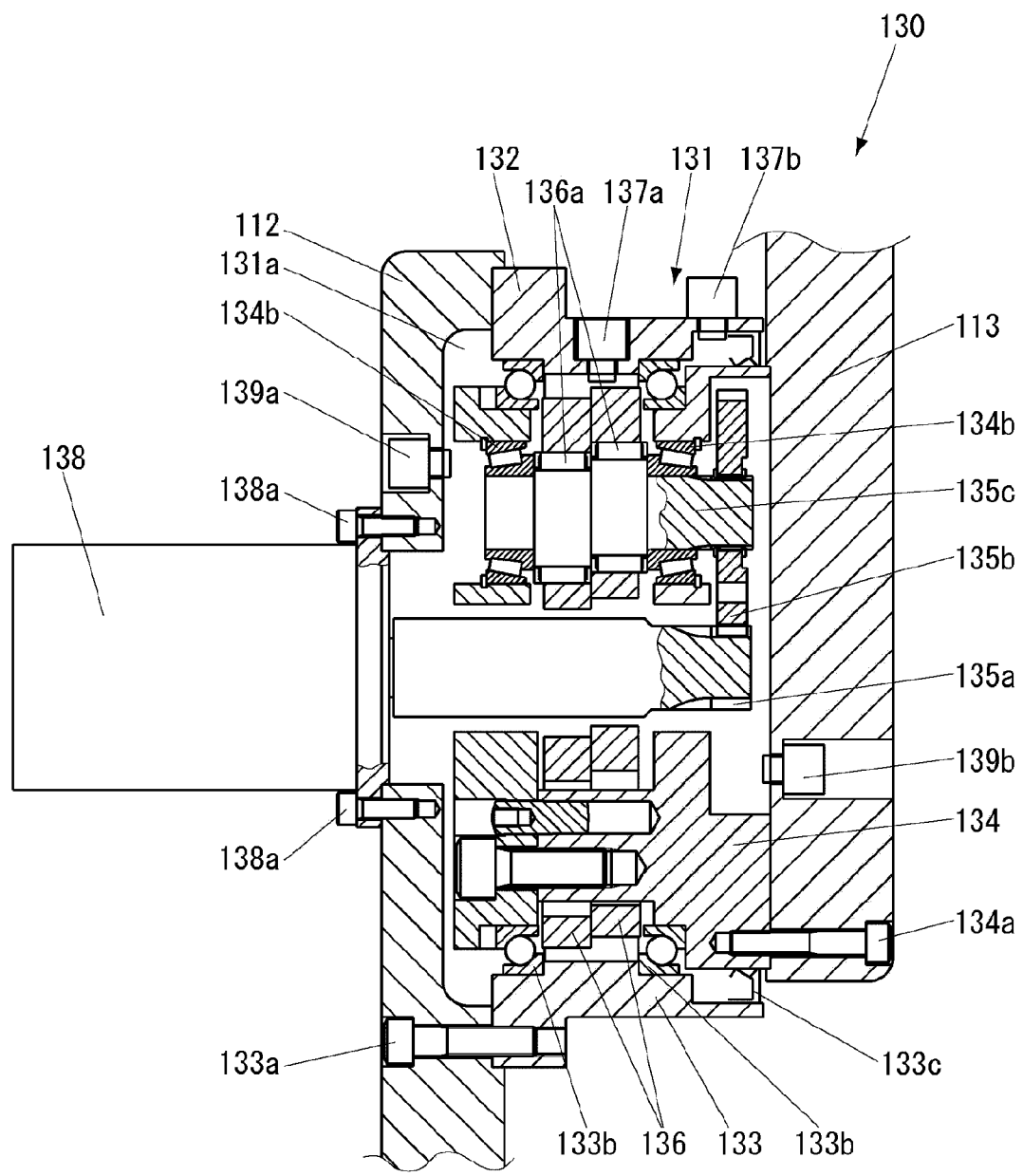
FIG. 2 is a cross sectional view of a joint of the industrial robot shown in FIG. 1.

FIG. 2 is a cross sectional view of the joint 130. Explanations are hereunder given to the joint 130. The same also applies to the joint 120 and the joints 140 to 170.

As shown in FIG. 2, the joint 130 is equipped with a speed reducer 131 to serve as a speed reducer for an industrial robot of the invention that joins the arm 112 to the arm 113; a motor 138 secured to the arm 112 by means of a bolt 138a; and a lubricant deterioration sensor 139a and a lubricant deterioration sensor 139b for detecting deterioration of a lubricant 131a of the speed reducer 131.

The speed reducer 131 is equipped with a speed reducer main body 132 and a lubricant deterioration sensor 137a and a lubricant deterioration sensor 137b for detecting deterioration of the lubricant 131a of the speed reducer main body 132.

The speed reducer main body 132 is equipped with a case 133 secured to the arm 112 with a bolt 133a; a support 134 secured to the arm 113 with a bolt 134a; a gear 135a fixed to an output shaft of the motor 138; three gears 135b that are placed at regular intervals around a center shaft of the speed reducer 131 and that mesh with the gear 135a; three crank shafts 135c that are placed at regular intervals around the center shaft of the decelerator 131 and that are secured to the respective gears 135b; and two external gears 136 that mesh with internal gears provided in the case 133.

The support 134 is rotatably supported by the case 133 by way of a bearing 133b. A seal member 133c for preventing a leakage of the lubricant 131a is interposed between the case 133 and the support 134.

The crank shafts 135c are rotatably supported by the support 134 by way of a bearing 134b and also rotatably supported by the external gears 136 by way of a bearing 136a.

The lubricant deterioration sensor 137a and the lubricant deterioration sensor 137b are secured to the case 133. The lubricant deterioration sensor 139a is secured to the arm 112. The lubricant deterioration sensor 139b is secured to the arm 113.

Figure 3:
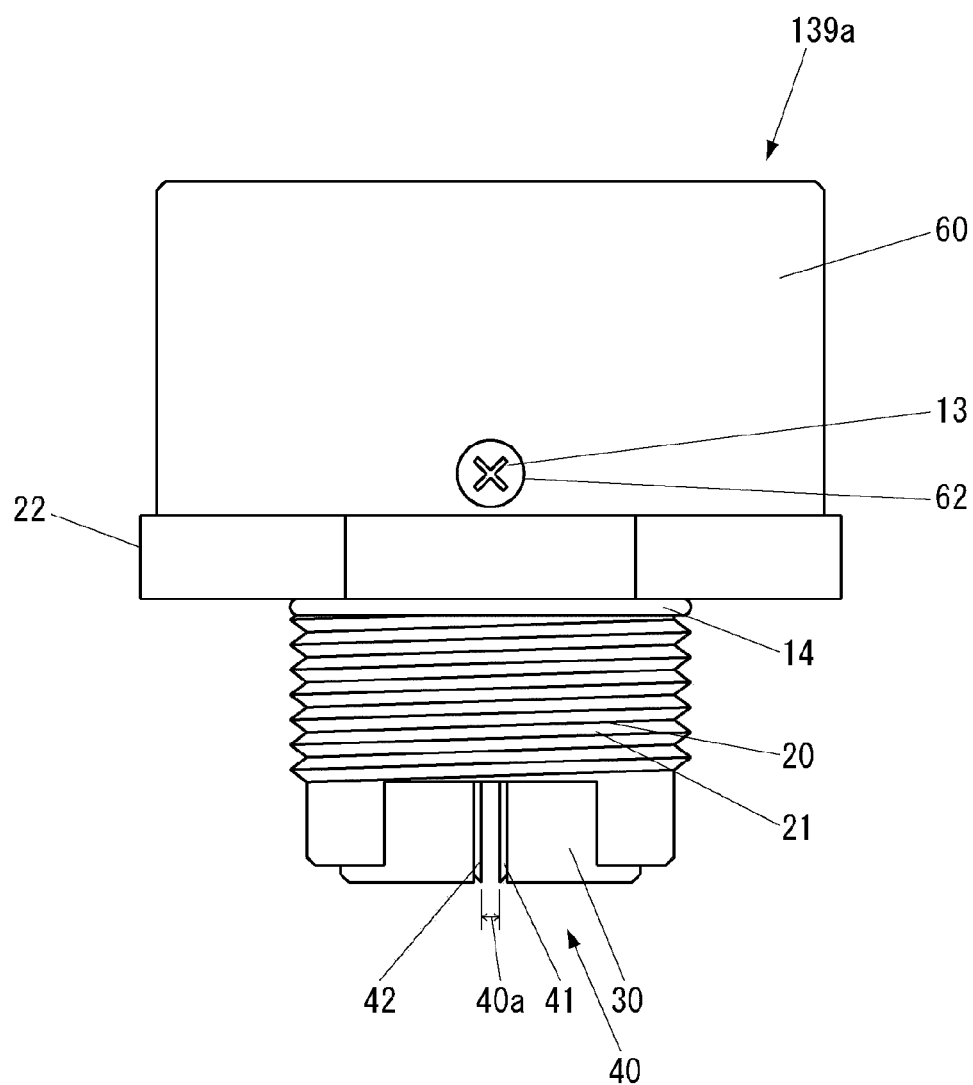
FIG. 3 is a front view of a lubricant deterioration sensor shown in FIG. 2.
Figure 4:
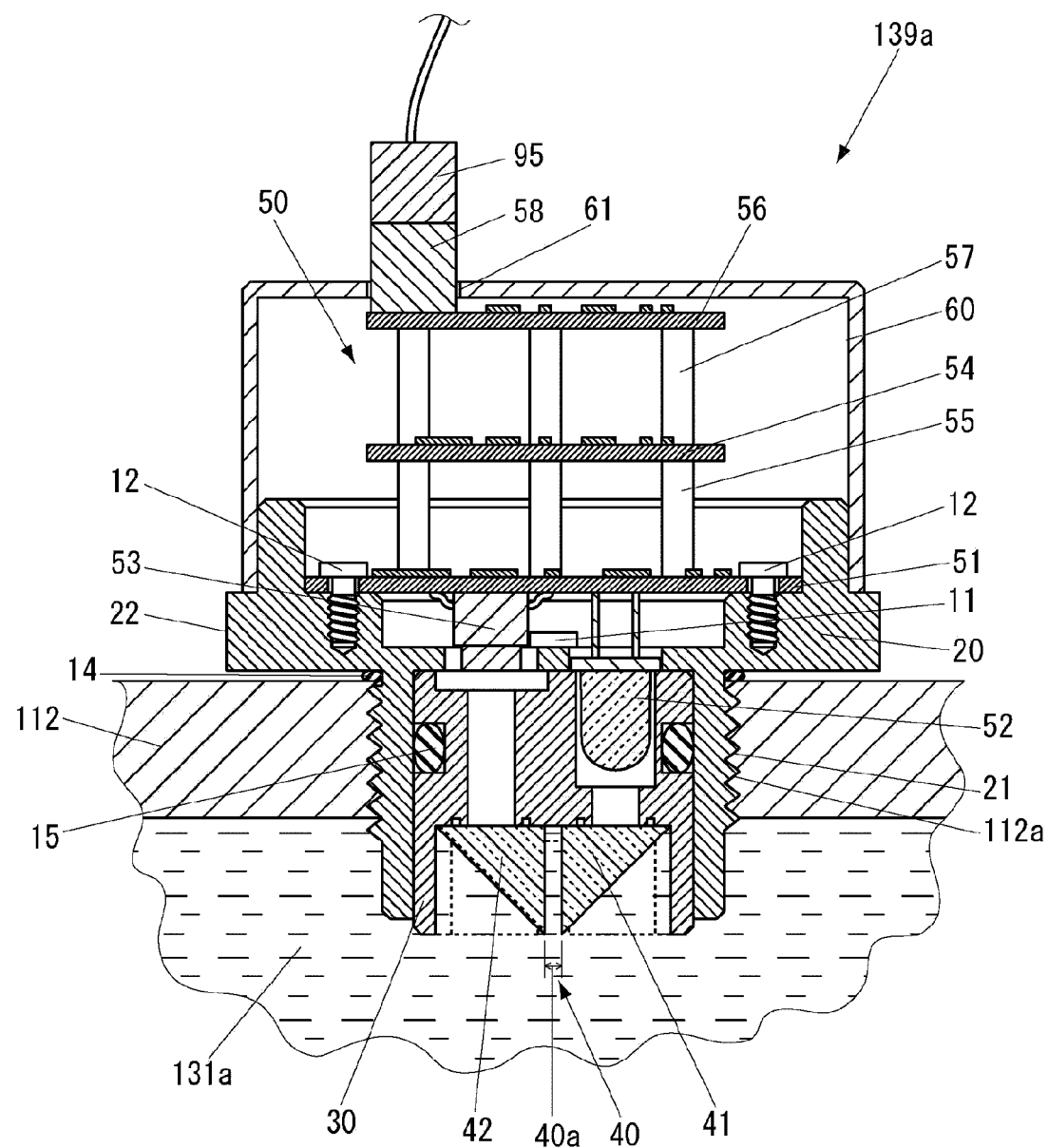
FIG. 4 is a front cross sectional view of the lubricant deterioration sensor shown in FIG. 3.

FIG. 3 is a front view of the lubricant deterioration sensor 139a. FIG. 4 is a front cross sectional view of the lubricant deterioration sensor 139a that remains secured to the arm 112. Explanations are hereunder given to the lubricant deterioration sensor 139a. However, the same also applies to lubricant deterioration sensors, such as the lubricant deterioration sensors 137a, 137b, and 139b, other than the lubricant deterioration sensor 139a.

As shown in FIGS. 3 and 4, the lubricant deterioration sensor 139a has a support member 20 that supports parts of the lubricant deterioration sensor 139a and that is made of an aluminum alloy; a holder 30 that is secured to the support member 20 with a screw 11 and that is made of an aluminum alloy; a clearance forming member 40 held by the holder 30; an electronic parts group 50 equipped with a circuit board 51 secured to the support member 20 with screws 12; and a cover 60 that is secured to the support member 20 with screws 13 and that is made of an aluminum alloy.

The clearance forming member 40 is made from two rectangular prisms 41 and 42 that are made of glass. An oil clearance 40a that is for intrusion of the lubricant 131a is formed between the two rectangular prisms 41 and 42.

The electronic parts group 50 is equipped with a white LED 52 implemented on the circuit board 51; an RGB sensor 53 implemented on the circuit board 51; a circuit board 54 placed opposite the surface of the circuit board 51 on which the white LED 52 and the RGB sensor 53 are implemented; a plurality of pillars 55 for fixing the circuit board 51 to the circuit board 54; a circuit board 56 placed opposite the side of the circuit board 54 that faces the circuit board 51; a plurality of pillars 57 for fixing the circuit board 54 to the circuit board 56; and a connector 58 implemented opposite the side of the circuit board 56 that faces the circuit board 54. A plurality of electronic parts are implemented on the circuit board 51, the circuit board 54, and the circuit board 56. The circuit board 51, the circuit board 54, and the circuit board 56 are electrically connected together.

The lubricant deterioration sensor 139a is equipped with an O ring 14 that prevents a leakage of the lubricant 131a from spacing between the support member 20 and the arm 112 and an O ring 15 that prevents a leakage of the lubricant 131a from spacing between the support member 20 and the holder 30.

Figure 5A:
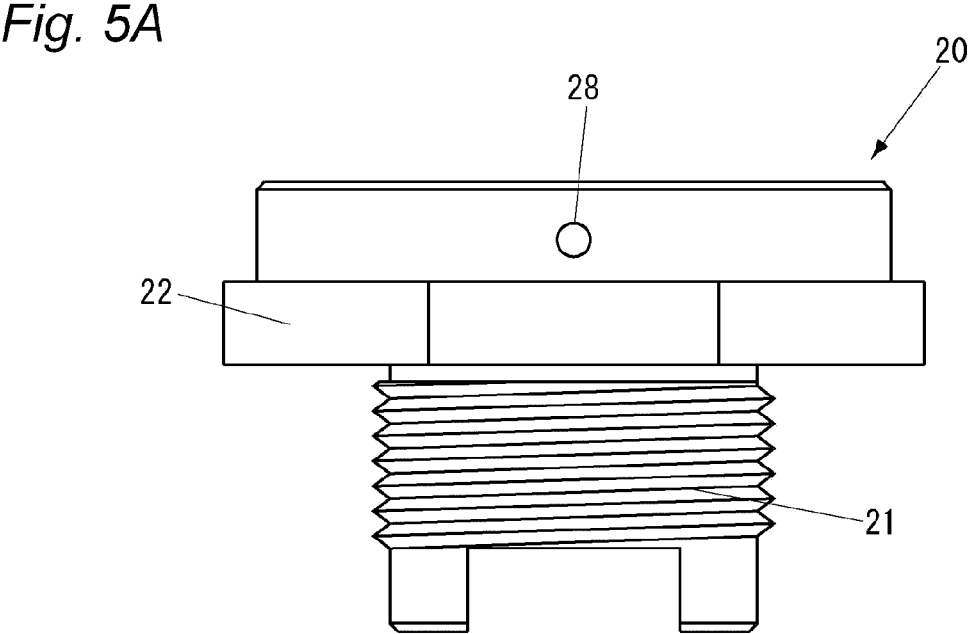
FIG. 5A is a front view of a support member shown in FIG. 3.
Figure 5B:
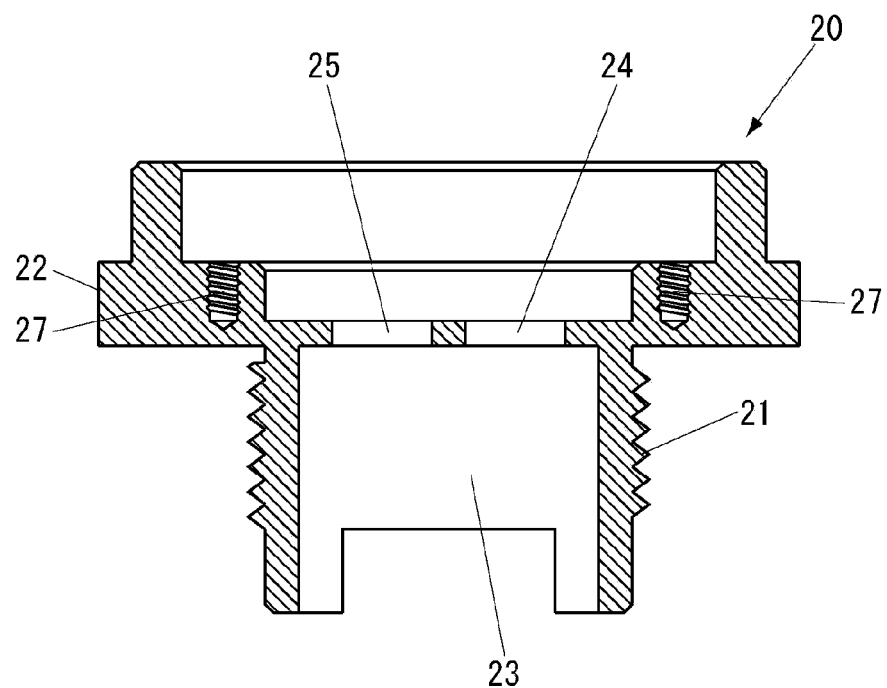
FIG. 5B is a front cross sectional view of the support member shown in FIG. 3.
Figure 6A:
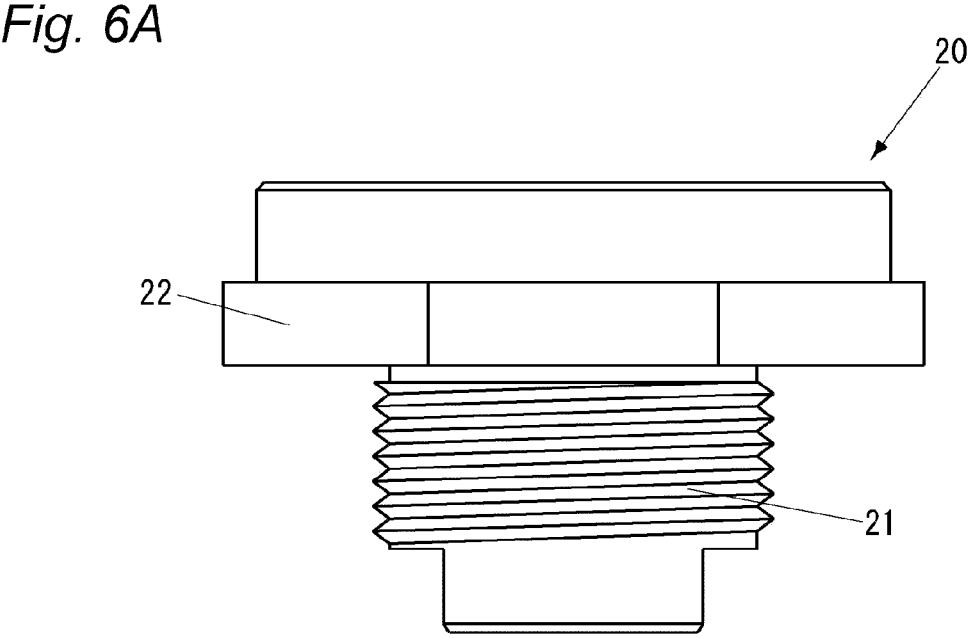
FIG. 6A is a side view of the support member shown in FIG. 3.
Figure 6B:
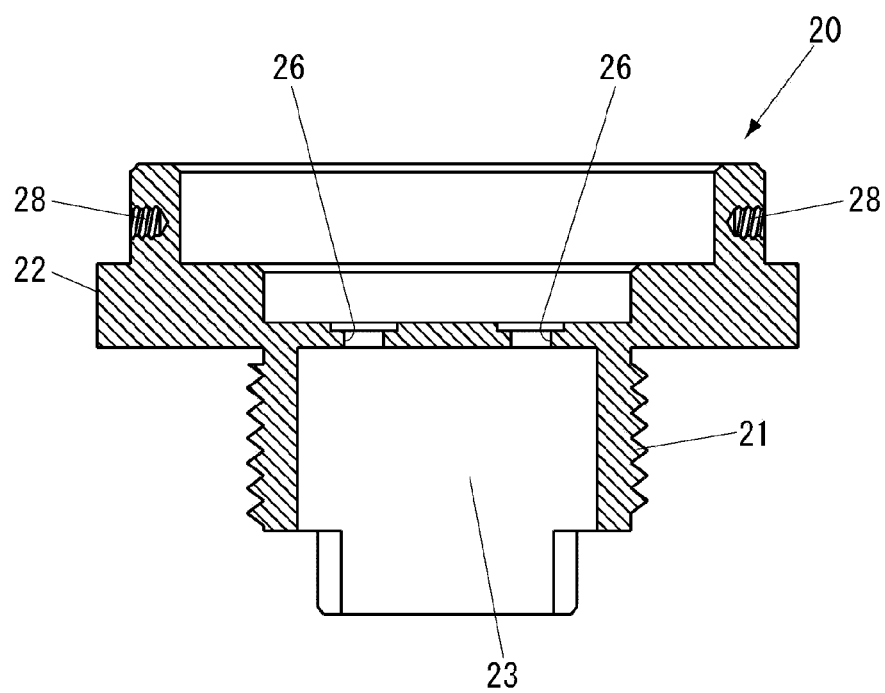
FIG. 6B is a side cross sectional view of the support member shown in FIG. 3.
Figure 7A:
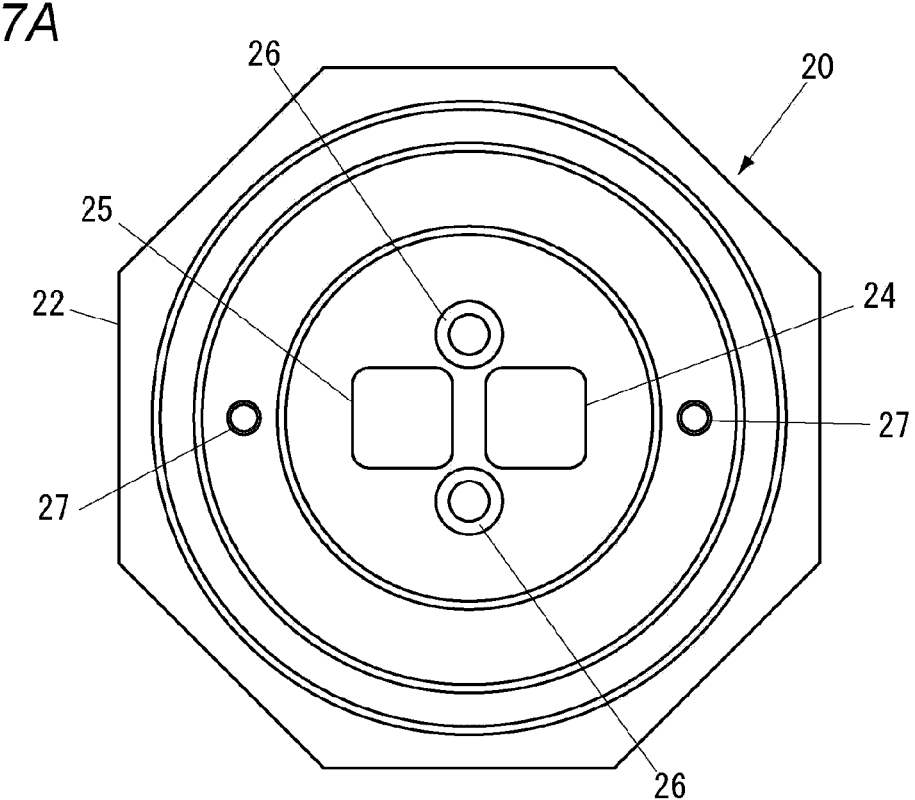
FIG. 7A is a plan view of the support member shown in FIG. 3.
Figure 7B:
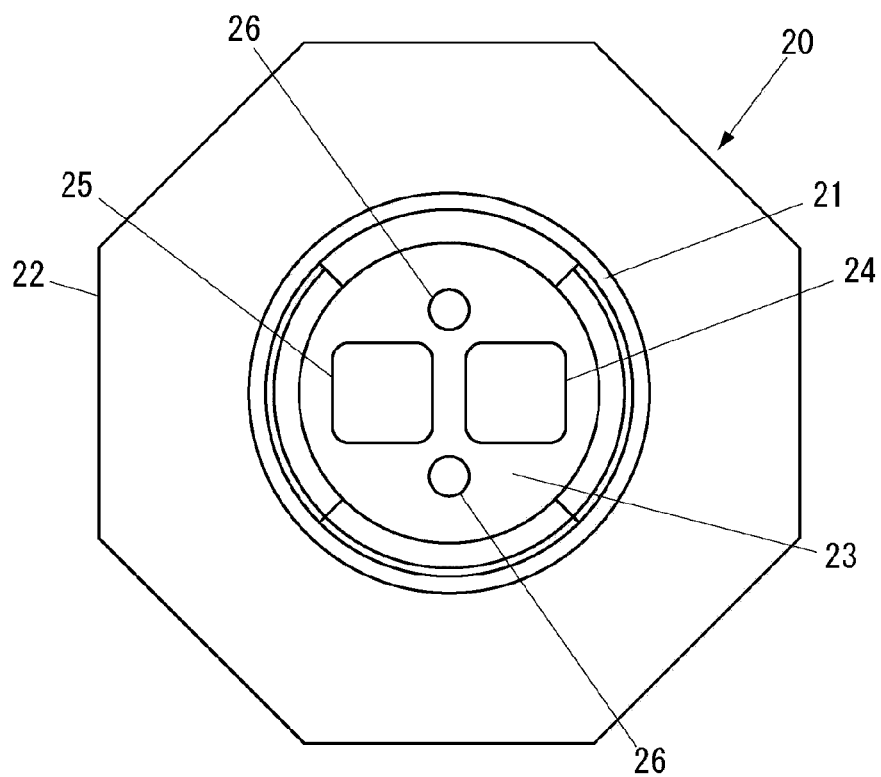
FIG. 7B is a bottom view of the support member shown in FIG. 3.

FIG. 5A is a front view of the support member 20. FIG. 5B is a front cross sectional view of the support member 20. FIG. 6A is a side view of the support member 20. FIG. 6B is a side cross sectional view of the support member 20. FIG. 7A is a plan view of the support member 20. FIG. 7B is a bottom view of the support member 20.

As shown in FIGS. 3 to 7B, the support member 20 is equipped with a screw portion 21 to be secured in a tapped hole 112a of the arm 112, a hexagonal tool contact 22 to be gripped by a tool when the screw portion 21 is rotated with respect to a tapped hole 112a of the arm 112, and a holder housing 23 that houses the holder 30. The support member 20 has a hole 24 for insertion of the white LED 52; a hole 25 for insertion of the RGB sensor 53; two holes 26 for insertion of the screw 11; two tapped holes 27 for insertion of the screws 12; and two tapped holes 28 for screw engagement with the screws 13.

The support member 20 supports the white LED 52 and the RGB sensor 53 by way of the circuit board 51. The support member 20 supports the clearance forming member 40 by way of the holder 30.

Figure 8A:
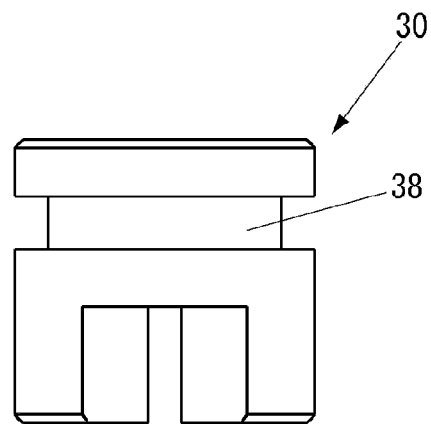
FIG. 8A is a front view of a holder shown in FIG. 3.
Figure 8B:
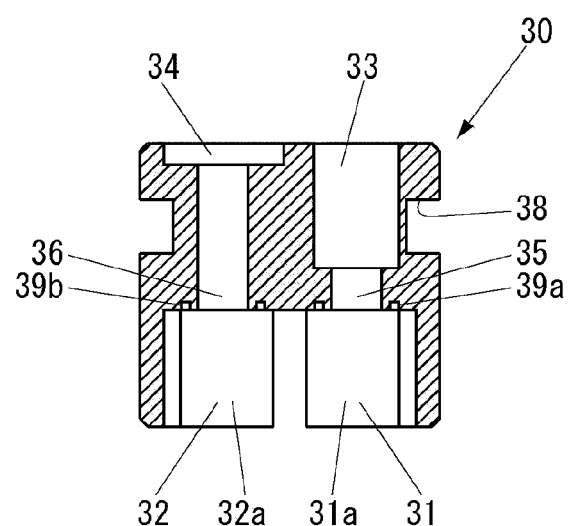
FIG. 8B is a front cross sectional view of the holder shown in FIG. 3.
Figure 9A:
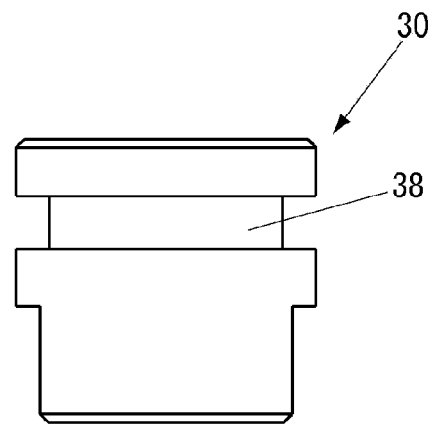
FIG. 9A is a side view of the holder shown in FIG. 3.
Figure 9B:
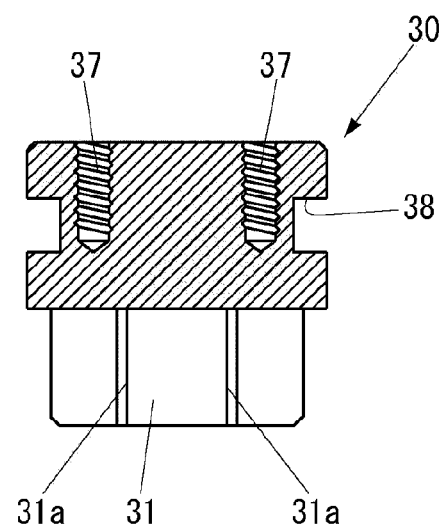
FIG. 9B is a side cross sectional view of the holder shown in FIG. 3.
Figure 10A:
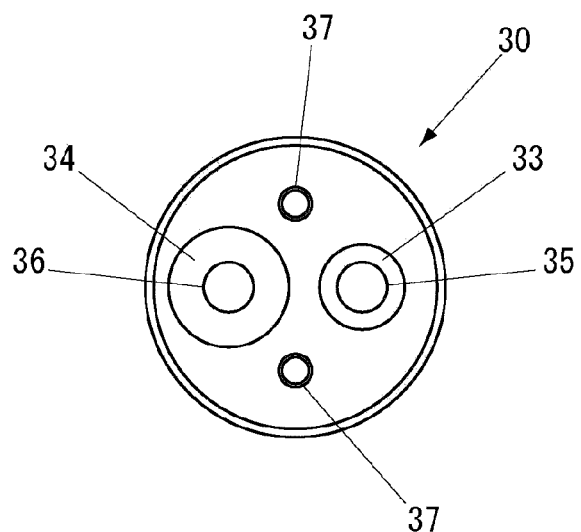
FIG. 10A is a plan view of the holder shown in FIG. 3.
Figure 10B:
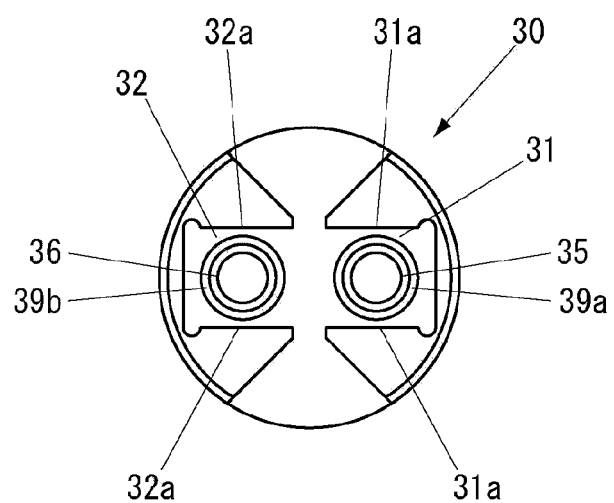
FIG. 10B is a bottom view of the holder shown in FIG. 3.
Figure 11:
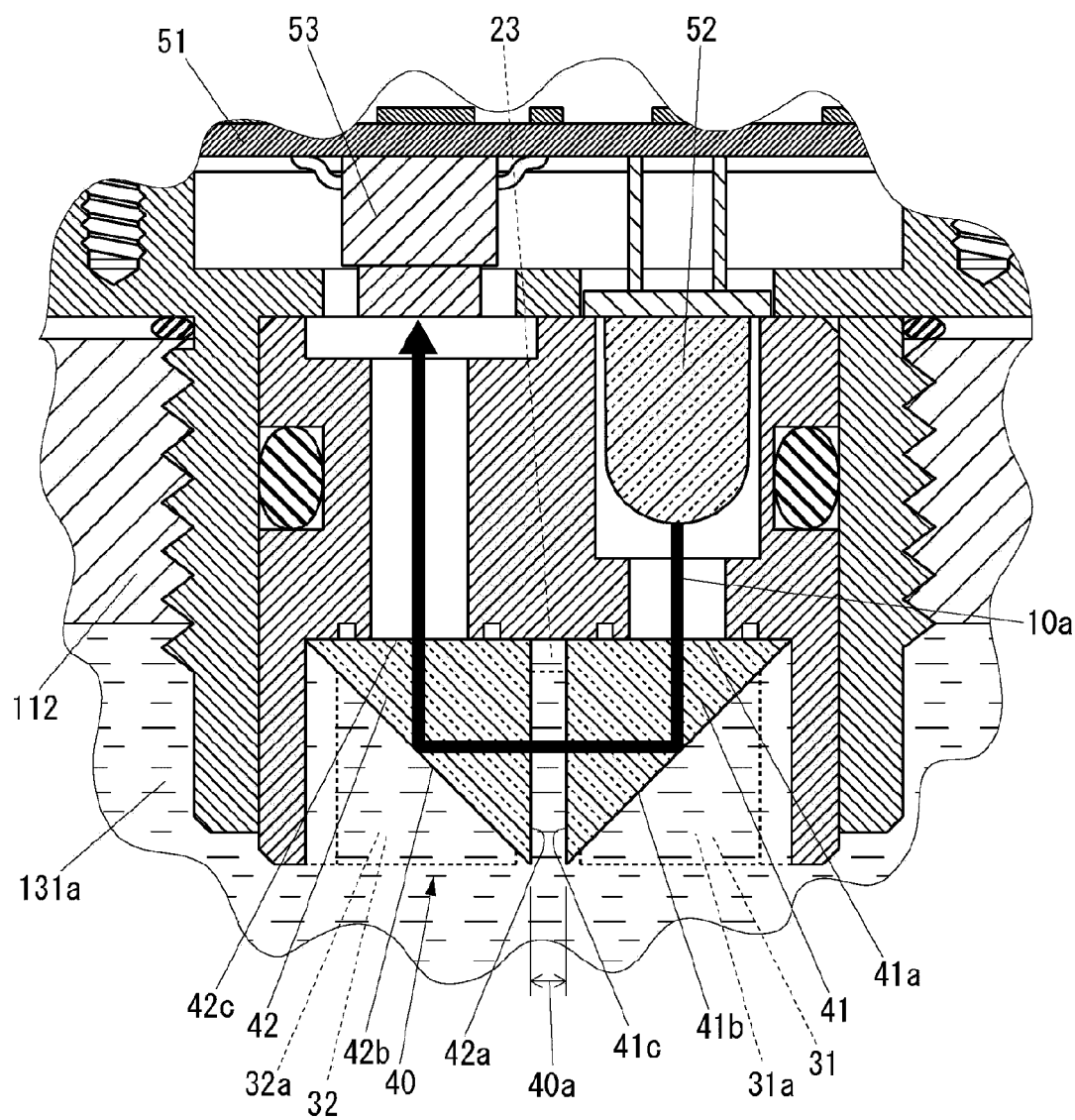
FIG. 11 is a diagram showing an optical path from a white LED to an RGB sensor shown in FIG. 4.

FIG. 8A is a front view of the holder 30. FIG. 8B is a front cross sectional view of the holder 30. FIG. 9A is a side view of the holder 30. FIG. 9B is a side cross sectional view of the holder 30. FIG. 10A is a plan view of the holder 30. FIG. 10B is a bottom view of the holder 30. FIG. 11 is a diagram showing an optical path 10a from the white LED 52 to the RGB sensor 53.

As shown in FIGS. 3, 4, and 8A to 11, the holder 30 is equipped with a prism housing 31 that houses the rectangular prism 41, a prism housing 32 that houses the rectangular prism 42, and an LED housing 33 that houses the white LED 52. Formed in the holder 30 are a hole 34 for the RGB sensor 53, a hole 35 for establishing a mutual communication between the prism housing 31 and the LED housing 33, a hole 36 for establishing a mutual communication between the prism housing 32 and the hole 34, two tapped holes 37 for screw engagement with the screws 11, a groove 38 to which the O ring 15 is to be fitted, an annular groove 39a for preventing intrusion of an adhesive, which is used for fixing the rectangular prism 41 to the prism housing 31, into the hole 35, and an annular groove 39b for preventing intrusion of an adhesive, which is used for fixing the rectangular prism 42 to the prism housing 32, into the hole 36.

The prism housing 31 has two walls 31a between which the rectangular prism 41 is to be inserted. The walls 31a fix the rectangular prism 41 by means of an adhesive. The prism housing 32 has two walls 32a between which the rectangular prism 42 is to be inserted. The walls 32a fix the rectangular prism 42 by means of an adhesive.

The holder 30 surrounds at least a portion of the optical path 10a from the white LED 52 to the RGB sensor 53 by means of the LED housing 33, the hole 35, the prism housing 31, the prism housing 32, the hole 36, the hole 34, making up an optical path surrounding member of the invention.

A surface of the holder 30 is treated by antireflection; for instance, mat black anodized aluminum treatment.

As shown in FIG. 11, the oil clearance 40a of the clearance forming member 40 is placed on the optical path 10a from the white LED 52 to the RGB sensor 53.

The rectangular prisms 41 and 42 are transmissive so that light emitted from the white LED 52 transmits therethrough. The rectangular prism 41 has an incident surface 41a on which light emitted by the white LED 52 falls, a reflection surface 41b that reflects the light fell on the incident surface 41a, to thus make a 90-degree turn of a traveling direction of light, and an exit surface 41c from which the light reflected by the reflection surface 41b exits. The rectangular prism 42 has an incident surface 42a on which light exited from the exit surface 41c of the rectangular prism 41 falls, a reflection surface 42b that reflects the light fell on the incident surface 42a, to thus make a 90-degree turn of a traveling direction of light, and an exit surface 42c from which the light reflected by the reflection surface 42b exits.

The incident surface 41a, the reflection surface 41b, and the exit surface 41c of the rectangular prism 41, and the incident surface 42a, the reflection surface 42b, and the exit surface 42c of the rectangular prism 42 are optically polished. The reflection surface 41b of the rectangular prism 41 and the reflection surface 42b of the rectangular prism 42 each are covered with an aluminum evaporated film. In order to protect the aluminum evaporated film that has a low degree of hardness and adhesion, the aluminum evaporated film is further coated with an SiO$_2$ film.

The optical path 10a is bent at 90-degree angle on the reflection surface 41b of the rectangular prism 41, further is bent at 90-degree angle also on the reflection surface 42b of the rectangular prism 42. To be specific, the optical path 10a is bent at 180 degrees angle by the clearance forming member 40.

A distance between the exit surface 41c of the rectangular prism 41 and the incident surface 42a of the rectangular prism 42 is a length of the oil clearance 40a. The length of the oil clearance 40a is 1 millimeter for instance. When the length of the oil clearance 40a is too short, contaminants in the lubricant 131a become difficult to flow through the oil clearance 40a appropriately, so that a degree of detection accuracy of a color of the contaminants in the lubricant 131a deteriorates. In the meantime, when the length of the oil clearance 40a is too long, light emitted from the white LED 52 is too absorbed by the contaminants in the lubricant 131a in the oil clearance 40a to reach the RGB sensor 53, so that the degree of detection accuracy of the color of the contaminants in the lubricant 131a also deteriorates. Consequently, it is preferable that the length of the oil clearance 40a be appropriately set such that the degree of detection accuracy of the color of the contaminants in the lubricant 131a improves.

The white LED 52 is an electronic part that emits white light and makes up a light emitting element of the invention. For instance, NSPW500GS-K1 manufactured by Nichia Corporation, can be used as the white LED 52.

The RGB sensor 53 is an electronic part that detects a color of received light and makes up a color light receiving element of the invention. For instance, S9032-02 manufactured by Hamamatsu Photonics K.K. can be used as the RGB sensor 53.

As shown in FIG. 4, the connector 58 is connected to a connector 59 of an external device of the lubricant deterioration sensor 139a and is fed with electric power from the external device by way of a connector 95. A detection result of the lubricant deterioration sensor 139a is output to the external device as an electric signal by way of the connector 95.

Figure 12A:
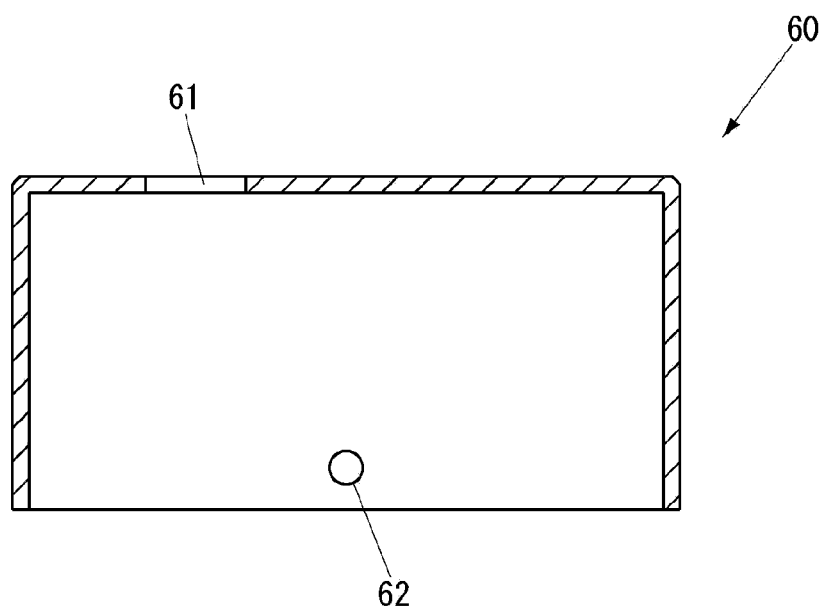
FIG. 12A is a front cross sectional view of a cover shown in FIG. 3.
Figure 12B:
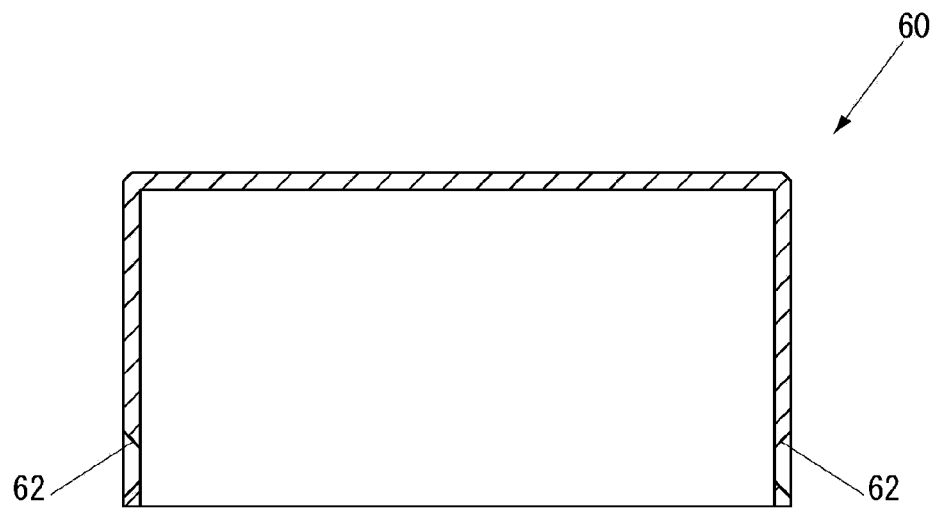
FIG. 12B is a side cross sectional view of the cover shown in FIG. 3.
Figure 13A:
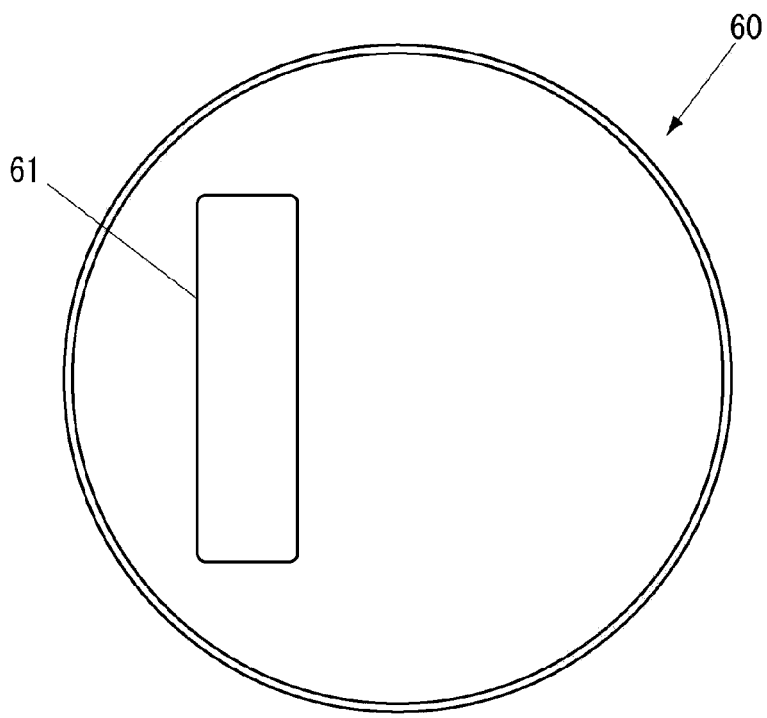
FIG. 13A is a plan view of the cover shown in FIG. 3.
Figure 13B:
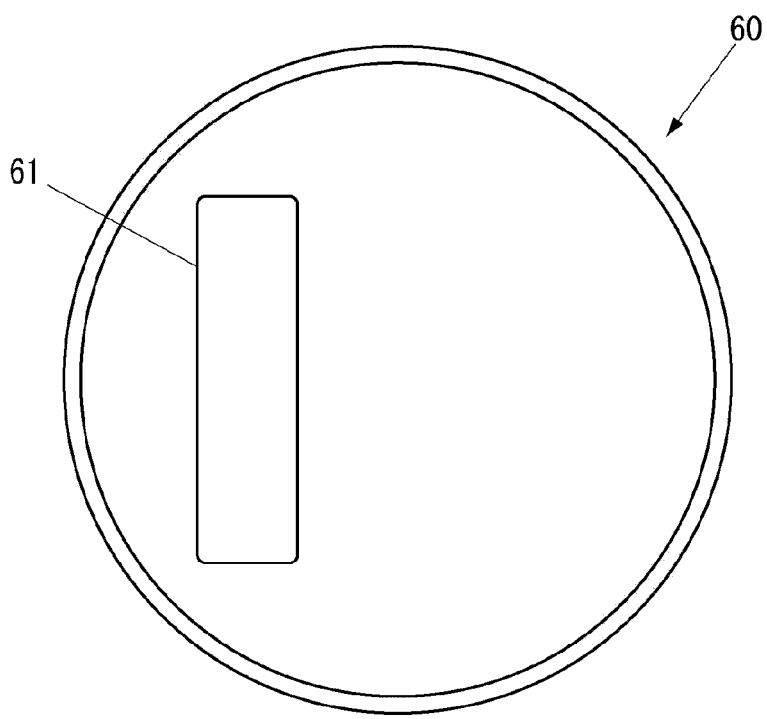
FIG. 13B is a bottom view of the cover shown in FIG. 3.

FIG. 12A is a front cross sectional view of the cover 60. FIG. 12B is a side cross sectional view of the cover 60. FIG. 13A is a plan view of the cover 60. FIG. 13B is a bottom view of the cover 60.

As shown in FIGS. 3, 4, 12, and 13, the cover 60 has a hole 61 for insertion of the connector 58 and two holes 62 for insertion of the screw 13.

A surface of the cover 60 is treated by antireflection; for instance, mat black anodized aluminum treatment.

Next, a method for assembling the lubricant deterioration sensor 139a is described. In this regard, explanations are given to the lubricant deterioration sensor 139a. However, the same also applies to a lubricant deterioration sensor other than the lubricant deterioration sensor 139a, such as the lubricant deterioration sensors 137a, 137b, and 139b.

First, an adhesive is applied to two surfaces of the surfaces of the rectangular prism 41 that contact the two walls 31a of the prism housing 31 as well as to an outer peripheral surface of the groove 39a that contacts the incident surface 41a of the rectangular prism 41 of the prism housing 31 of the holder 30, whereby the rectangular prism 41 is secured to the prism housing 31 by means of the adhesive. In addition, an adhesive is applied to two surfaces of the surfaces of the rectangular prism 42 that contact the two walls 32a of the prism housing 32 as well as to an outer peripheral surface of the groove 39b which contacts the exit surface 42c of the rectangular prism 42 of the prism housing 32 of the holder 30, whereby the rectangular prism 42 is secured to the prism housing 32 by means of the adhesive. Further, the white LED 52 is secured to the LED housing 33 of the holder 30 by means of the adhesive.

Next, the holder 30 outfitted with the O ring 15 is secured, by means of the screw 11, to the holder housing 23 of the support member 20 outfitted with the O ring 14.

The electronic parts group 50 into which various electronic parts except the white LED 52; namely, the circuit board 51, the RGB sensor 53, and the connector 58, are previously assembled is secured to the support member 20 by the screws 12, thereby the white LED 52 is soldered to the circuit board 51.

Finally, the cover 60 is secured to the support member 20 by the screw 13.

A method for mounting the lubricant deterioration sensor 139a to the arm 112 is now described. Although an explanation is given to the lubricant deterioration sensor 139a in the following descriptions, the same also applies to their counterpart lubricant deterioration sensors, such as the lubricant deterioration sensors 137a, 137b, and 139b, other than the lubricant deterioration sensor 139a.

First, the tool contact 22 of the support member 20 is pinched with a tool, and the screw 21 of the support member 20 is screwed into the tapped hole 112a of the arm 112, whereby the lubricant deterioration sensor 139a is secured to the arm 112.

The connector 95 of an external device of the lubricant deterioration sensor 139a is connected to the connector 58.

Operation of the industrial robot 100 is now described.

First, operation of the joint 130 is described. Although the joint 130 is described in the followings, the same also applies its counterpart joints 120 and 140 to 170.

When an output shaft of the motor 138 of the joint 130 rotates, torque of the motor 138 is decelerated by the speed reducer 131, whereupon the arm 113 secured to the support 134 of the speed reducer 131 is actuated with respect to the arm 112 secured to the case 133 of the speed reducer 131.

Next, operation of the lubricant deterioration sensor 139a is described. Although explanations are given to the lubricant deterioration sensor 139a in the followings, the same also applies to its counterpart lubricant deterioration sensors, such as the lubricant deterioration sensors 137a, 137b, and 139b, other than the lubricant deterioration sensor 139a.

In the lubricant deterioration sensor 139a, white light is emitted from the white LED 52 by means of the electric power fed from an external device by way of the connector 58.

The lubricant deterioration sensor 139a outputs amounts of RGB colors of light received by the RGB sensor 53 as an electric signal to an external device by way of the connector 58.

The lubricant deterioration sensor 139a can also be separately equipped with a sensor other than the RGB sensor 53. For instance, when a temperature sensor for detecting a temperature of the lubricant 131a is included in the electronic parts group 50, the lubricant deterioration sensor 139a can output a temperature detected by the temperature sensor to an external device as an electric signal by way of the connector 58.

As described above, the respective lubricant deterioration sensors, like the lubricant deterioration sensor 139a, detect colors from light of, among white light rays emitted from the white LED 52, wavelengths that are not absorbed by contaminants in the lubricant 131a in the oil clearance 40a by use of the RGB sensor 53, so that colors of the contaminants in the lubricant 131a of the speed reducer 131 can be instantly detected. In other words, the respective lubricant deterioration sensors can instantly specify, on the basis of the colors detected by the RGB sensor 53, types and amounts of contaminants in the lubricant 131a of the speed reducer 131 by use of an external device, like a computer. Therefore, the respective speed reducers, such as the speed reducer 131, and the industrial robot 100 can instantly predict occurrence of a failure. In relation to the respective lubricant deterioration sensors, electronic parts that specify types and amounts of contaminants in lubricants from the colors detected by the RGB sensor 53 can also be included in the electronic parts group 50.

The lubricant 131a is often doped with various additives; for instance, a friction reducer intended for reducing friction on a friction surface, such as organic molybdenum like MoDTC and MoDTP; an extreme pressure additive, like an SP-based additive, intended for enhancing an extreme pressure characteristic, i.e., a capability of inhibiting seizure of the friction surface; and a dispersing agent, like Ca sulfonate, intended for inhibiting occurrence and adhesion of sludge. The additives settle out and are separated from the lubricant 131a with a progress in deterioration of the lubricant 131a. Specifically, a decrease in the amounts of additives in the lubricant 131a can be utilized for predicting occurrence of a failure in the speed reducers or the industrial robot 100. In addition to specifying the amount of iron powder in the lubricant 131a, the respective lubricant deterioration sensors can also specify, from detected colors, a degree of deterioration of base oil that is a concomitant of a reduction in the amounts of additives added to the lubricant 131a and an increase in amounts of contaminants, such as sludge. Therefore, when compared with the related art technique that enables prediction of occurrence of a failure in the speed reducers only on the basis of a concentration of iron powder, the speed reducers and the industrial robot 100 can enhance a degree of accuracy of prediction of a prediction.

In each of the lubricant deterioration sensors, the light emitting element is a white LED that emits white light. For this reason, when compared with a configuration in which the light emitting elements are lamps other than the LED, the sensors can be miniaturized. Therefore, the respective speed reducers and the industrial robot 100 can be miniaturized. In this respect, the light emitting element of the invention also includes an element other than the white LED. For instance, the light emitting element may also be a lamp other than an LED. Also, the light emitting element can also include a red LED or a red lamp other than the LED, a green LED or a green lamp other than the LED, a blue LED or a blue lamp other than the LED, and white light can be emitted by a combination of colors of light emitted from the LEDs or colors of light emitted from the lamps other than the LEDs.

In each of the lubricant deterioration sensors, the reflection surfaces 41b and 42b for bending the optical path 10a are formed on the clearance forming member 40. Therefore, when compared with the configuration in which the optical path 10a from the white LED 52 to the RGB sensor 53 is straightforward, the entirety of the sensor can be miniaturized by placing the white LED 52 and the RGB sensor 53 in close proximity to each other. Further, in each of the lubricant deterioration sensors, the clearance forming member 40 plays the role of bending the optical path 10a as well as the role of creating the oil clearance 40a. Hence, when compared with a configuration separately provided with a member for bending the optical path 10a instead of the clearance forming member 40, the number of parts can be curtailed. Consequently, the speed reducers and the industrial robot 100 can be miniaturized and subjected to a decrease in the number of parts.

In particular, in each of the lubricant deterioration sensors, the clearance forming member 40 is made up of the two rectangular prisms 41 and 42 on which there are formed the reflection surfaces 41b and 42b for effecting 90-degree refraction of the optical path 10a. The optical path 10a is subjected to 180-degree refraction by means of the reflection surfaces 41b and 42b of the two rectangular prisms 41 and 42, and the oil clearance 40a is created between the two rectangular prisms 41 and 42. Hence, the lubricant deterioration sensor can be miniaturized by means of a simple configuration that includes a smaller number of parts. Consequently, the respective speed reducers and the industrial robot 100 can be miniaturized by means of a simple configuration that includes a smaller number of parts.

Each of the lubricant deterioration sensors is equipped with the holder 30 that surrounds at least a portion of the optical path 10a. The surface of the holder 30 is treated with antireflection processing. Hence, the RGB sensor 53 can be prevented from experiencing unwanted reflected light. Hence, when compared with the configuration in which the RGB sensor 53 experiences unwanted reflected light, each of the lubricant deterioration sensors can enhance the detection accuracy of colors of contaminants in the lubricant 131a. Therefore, the respective speed reducers and the industrial robot 100 can enhance the accuracy of prediction of a failure.

In each of the lubricant deterioration sensors, the surfaces of the clearance forming member 40 that create the oil clearance 40a; namely, the exit surface 41c of the rectangular prism 41 and the incident surface 42a of the rectangular prism 42, can also be subjected to oil repellent treatment. In relation to each of the lubricant deterioration sensors, when the exit surface 41c of the rectangular prism 41 and the incident surface 42a of the rectangular prism 42 are given oil repellent treatment, the lubricant 131a can easily flow through the oil clearance 40a. Therefore, when compared with a configuration in which the lubricant 131a becomes easily congested in the oil clearance 40a, the detection accuracy of colors of contaminants in the lubricant 131a can be enhanced. Moreover, in relation to each of the lubricant deterioration sensors, when the exit surface 41c of the rectangular prism 41 and the incident surface 42a of the rectangular prism 42 are given oil repellent treatment, the exit surface 41c of the rectangular prism 41 and the incident surface 42a of the rectangular prism 42 become less susceptible to stains, so that degradation of detection accuracy of colors of contaminants in the lubricant 131a, which would otherwise be caused by adhesion of stains on the exit surface 41c and the incident surface 42a, can be inhibited. Therefore, the respective speed reducers and the industrial robot 100 can enhance the accuracy of prediction of a failure.

In each of the lubricant deterioration sensors, the layout of the white LED 52 and the RGB sensor 53 may also be different from that described in connection with the embodiment. For instance, in each of the lubricant deterioration sensors, the optical path 10a from the white LED 52 to the RGB sensor 53 may also be straightforward.

In each of the lubricant deterioration sensors, the optical path 10a can also be refracted by means of a configuration other than the rectangular prism.

In each of the lubricant deterioration sensors, a battery; for instance, a cell, can also be used as power supply means, and wireless communication; for instance, can also be used as means for outputting a detection result to an external device.

The locations where the respective lubricant deterioration sensors are installed are not restricted to those described in connection with the embodiment. It is preferable that the locations be set as appropriate in accordance with applications of the industrial robot 100.

The patent application is based on Japanese Patent Application JP-2010-269097 (filed on Dec. 2, 2010) and Japanese Patent Application JP-2011-3853 (filed on Jan. 12, 2011), the subject matters of which are incorporated herein by reference in their entireties.

INDUSTRIAL APPLICABILITY

The speed reducer for an industrial robot according to the present invention enables instant prediction of a failure.

REFERENCE SIGNS LIST

10*a* OPTICAL PATH
20 SUPPORT MEMBER
30 HOLDER (OPTICAL PATH SURROUNDING MEMBER)
40 CLEARANCE FORMING MEMBER
40*a* OIL CLEARANCE
41 RECTANGULAR PRISM
41*b* REFLECTION SURFACE
41*c* EXIT SURFACE (SURFACE THAT MAKES UP OIL CLEARANCE)
42 RECTANGULAR PRISM
42*a* ENTRANCE SURFACE (SURFACE THAT MAKES UP CLEARANCE)
42*b* REFLECTION SURFACE
52 WHITE LED (LIGHT EMITTING ELEMENT)
53 RGB SENSOR (COLOR RECEIVING ELEMENT)
100 INDUSTRIAL ROBOT
112 TO 116 ARM
120, 130, 140, 150, 160, 170 JOINT
131 SPEED REDUCER (SPEED REDUCER FOR INDUSTRIAL ROBOT)
131*a* LUBRICANT
132 SPEED REDUCER MAIN BODY
137*a*, 137*b*, 139*a*, 139*b* LUBRICANT DETERIORATION SENSOR

The invention claimed is:

1. A speed reducer for an industrial robot, comprising:
a speed reducer main body having a lubricant, the speed reducer main body is formed with an engageable portion; and
a lubricant deterioration sensor to detect deterioration of the lubricant in the speed reducer main body, wherein
the lubricant deterioration sensor includes
  a light emitting element to emit light,
  a color light receiving element to detect a color of received light,
  a clearance forming member forming an oil clearance in which the lubricant enters, and
  a support member supporting the light emitting element, the color light receiving element, and the clearance forming member,
the clearance forming member being light-transmissive so that the light emitted from the light emitting element is transmittable therethrough,
the oil clearance is provided on an optical path from the light emitting element to the color light receiving element,
a reflection surface for bending the optical path is formed on the clearance forming member,
the clearance forming member has two rectangular prisms each of which has the reflection surface for bending part of the optical path at 90-degree angle, so that the entire optical path is bent at 180-degree angle by the reflection surfaces of the two rectangular prisms,
the oil clearance is formed between the two rectangular prisms,
the support member includes an engaging portion and a tool contact portion,
the engageable portion of the speed reducer main body is formed through the speed reducer main body such that a tool is engageable with the tool contact portion from outside of the speed reducer main body, so that the engaging portion of the support member is secured to the engageable portion of the speed reducer main body thereby said lubricant deterioration sensor is fixed onto the speed reducer main body,
when said lubricant deterioration sensor is fixed onto the speed reducer main body, the oil clearance is positioned further inwardly from the internal surface of the speed reducer main body; and
a groove surrounding an opening of a space on the optical path between the light emitting element and the clearance forming member is formed on a surface of the support member to which the clearance forming member is attached so as to prevent an adhesive entering into the space.

2. The speed reducer for an industrial robot according to claim 1, wherein the light emitting element is a white LED configured to emit white light.

3. The speed reducer for an industrial robot according to claim 1, further comprising:
an optical path surrounding member for surrounding at least a portion of the optical path,
wherein a surface of the optical path surrounding member is treated with antireflection processing.

4. The speed reducer for an industrial robot according to claim 1, wherein the surfaces of the clearance forming member that forms the oil clearance are treated with oil repellent treatment.

5. The speed reducer for an industrial robot according to claim 1, wherein the support member further includes a tool contact portion and said engaging portion is a screw portion and said engageable portion is a tapped hole formed through the speed reducer main body.

6. The speed reducer for an industrial robot according to claim 5, wherein said tool contact portion is disposed outside of the speed reducer main body such that a tool is engageable with the contact portion from outside of the speed reducer main body.

7. The speed reducer for an industrial robot according to claim 1, wherein the tool contact portion has an outer diameter larger than an outer diameter of the engaging portion so that an O-ring is engaged on the engaging portion located between the tool contact portion and the engageable portion.

8. An industrial robot comprising:
an arm;
a speed reducer, having a lubricant disposed therein, for a joint of the arm; and
a lubricant deterioration sensor to detect deterioration of the lubricant of the speed reducer, wherein
the lubricant deterioration sensor has
  a light emitting element to emit light,
  a color light receiving element to detect a color of received light,
  a clearance forming member forming an oil clearance in which the lubricant enters, and a support member supporting the light emitting element, the color light receiving element, and the clearance forming member, the clearance forming member being light-transmissive so that the light emitted from the light emitting element is transmittable therethrough, the oil clearance is provided on an optical path from the light emitting element to the color light receiving element, a reflection surface for bending the optical path is formed on the clearance forming member, the clearance forming member has two rectangular prisms each of which has the reflection surface for bending part of the optical path at 90-degree angle, so that the entire optical path is bent at 180-degree angle by the reflection surfaces of the two rectangular prisms, the oil clearance is formed between the two rectangular prisms, said speed reducer includes a main body which has a support member formed with an engageable portion and said lubricant deterioration sensor is formed with an engaging portion, the support member includes an engaging portion and a tool contact portion, the support member includes an engaging portion and a tool contact portion, the engageable portion of the main body of the speed reducer is formed through the main body such that a tool is engageable with the tool contact portion from outside of the main body, so that the engaging portion of the support member is secured to the engageable portion of the main body thereby said lubricant deterioration sensor is fixed onto the speed reducer main body, when said lubricant deterioration sensor is fixed onto the speed reducer main body, the oil clearance is positioned further inwardly from the internal surface of the speed reducer main body; and a groove surrounding an opening of a space on the optical path between the light emitting element and the clearance forming member is formed on a surface of the support member to which the clearance forming member is attached so as to prevent an adhesive entering into the space.

9. The speed reducer for an industrial robot according to claim 8, wherein the support member further includes a tool contact portion and said engaging portion is a screw and said engageable portion is a tapped hole formed through the speed reducer main body.

10. The speed reducer for an industrial robot according to claim 9, wherein said tool contact portion is disposed outside of the speed reducer main body such that a tool is engageable with the contact portion from outside of the speed reducer main body.

11. The speed reducer for an industrial robot according to claim 8, wherein the tool contact portion has an outer diameter larger than an outer diameter of the engaging portion so that an O-ring is engaged on the engaging portion located between the tool contact portion and the engageable portion.

12. A speed reducer for an industrial robot, comprising:
a speed reducer main body having a lubricant and formed with an engageable portion; and
a lubricant deterioration sensor to detect deterioration of the lubricant in the speed reducer main body, wherein
the lubricant deterioration sensor includes:
  a light emitting element to emit light,
  a color light receiving element to detect a color of received light,
  a clearance forming member forming an oil clearance in which the lubricant enters, and
  a support member supporting the light emitting element, the color light receiving element, and the clearance forming member,
the clearance forming member being light-transmissive so that the light emitted from the light emitting element is transmittable therethrough,
the oil clearance is provided on an optical path from the light emitting element to the color light receiving element,
a reflection surface for bending the optical path is formed on the clearance forming member,
a holder with anti-reflection treatment, provided inside of the support member, said holder surrounds at least a portion of the optical path;
the clearance forming member has two rectangular prisms, each of t which has the reflection surface for ending part of the optical path at a 90-degree angle, so that the entire optical path is bent at 180-degree angle by the reflection surfaces of the two rectangular prisms,
the oil clearance is formed between the two rectangular prisms,
the support member includes an engaging portion and a tool contact portion,
the engageable portion of the speed reducer main body is formed through the speed reducer main body such that a tool is engageable with the tool contact portion from outside of the speed reducer main body, so that the engaging portion of the support member is secured to the engageable portion of the speed reducer main body thereby said lubricant deterioration sensor is fixed onto the speed reducer main body,
when said lubricant deterioration sensor is fixed onto the speed reducer main body, the oil clearance is positioned further inwardly from the internal surface of the speed reducer main body; and
a groove surrounding an opening of a space on the optical path between the light emitting element and the clearance forming member is formed on a surface of the holder to which the clearance forming member is attached so as to prevent an adhesive entering into the space.

13. The speed reducer for an industrial robot according to claim 12, wherein the tool contact portion has an outer diameter larger than an outer diameter of the engaging portion so that an O-ring is engaged on the engaging portion located between the tool contact portion and the engageable portion.

* * * * *